United States Patent [19]

Comstock et al.

[11] Patent Number: 4,769,445

[45] Date of Patent: Sep. 6, 1988

[54] PROCESS FOR THE SOLID PHASE SYNTHESIS OF PEPTIDES WHICH CONTAIN SULFATED TYROSINE

[75] Inventors: Jeanne Comstock; James D. Rosamond, both of Rochester, N.Y.

[73] Assignee: Pennwalt Corporation, Philadelphia, Pa.

[21] Appl. No.: 129,379

[22] Filed: Nov. 24, 1987

Related U.S. Application Data

[63] Continuation of Ser. No. 707,975, Mar. 4, 1985, abandoned, which is a continuation-in-part of Ser. No. 607,485, May 7, 1984, abandoned.

[51] Int. Cl.$^4$ .............................................. A61K 37/02
[52] U.S. Cl. ..................................... 530/333; 530/327; 530/328
[58] Field of Search ........................ 530/327, 328, 333

[56] References Cited

U.S. PATENT DOCUMENTS

| | | | |
|---|---|---|---|
| 3,038,908 | 6/1962 | Beereloom | 260/346.2 |
| 3,579,494 | 5/1971 | Ondetti et al. | 260/112.5 R |
| 3,705,140 | 12/1972 | Bernardi et al. | 260/112.5 R |
| 3,714,140 | 1/1973 | Sipos | 260/112.5 R |
| 3,723,406 | 3/1973 | Ondetti et al. | 260/112.5 R |
| 3,778,429 | 12/1973 | Ondetti et al. | 260/112.5 R |
| 3,839,315 | 10/1974 | Ondetti et al. | 260/112.5 R |
| 3,892,726 | 7/1975 | Ondetti et al. | 260/112.5 R |
| 4,076,913 | 2/1978 | Walker et al. | 525/54.11 |
| 4,102,878 | 7/1978 | Penke et al. | 260/112.5 R |
| 4,330,466 | 5/1982 | Yanaihara et al. | 260/112.5 R |
| 4,490,364 | 12/1984 | Rivier et al. | 424/177 |

OTHER PUBLICATIONS

Ondetti et al., Synthesis of Cholecystokinin-Pancreozymin. I, The C. Terminal Do Decapeptide, J.A.C.S., 92, pp. 195-199, (1970).

Pluscec et al., Synthesis of Analogs of the C-Terminal Octapeptide of Cholecystokinin-Pancreozymin Structure-Activity Relationship, J. Med. Chem. 13, pp. 349-352, (1970).

Gandreau et al., Solid-Phase Synthesis of COOH-Terminal Fragments of Cholecystokinin, Peptides, Rich & Gross Eds., pp. 193-195, (1981).

Crawley et al., The Role of Central and Peripheral Cholecystokinin in Mediating Appetitive Behaviors, Peptides, 3, pp. 535-538, (1982).

Penke et al., New Synthetic Approach to Peptide Sulfate Esters Syntesis and Biological Activities of CCK Analogs Abstr. Book for eighth American Peptide Symposium, p. 45, May 22-23, (1983).

Barany et al., Solid-Phase Peptide Synthesis, the Peptides Analysis, Synthesis, Biology, Chapter I, vol. 2, Gross & Melenhofer Ed., pp. 1-11, 65-67, 77-79.

Primary Examiner—Delbert R. Phillips
Assistant Examiner—Nathan M. Nutter

[57] ABSTRACT

Peptides and Peptide amides such as cholecystokinin (CCK-8) are synthesized in improved yields and purity by a solid phase process. The requisite protected peptide is elaborated and sulfated on a solid support, deprotected, and cleaved from the solid support to give the total synthesis of CCK-8 on a solid support. Thereafter, the peptide is purified in a single step by ion exchange chromatography to provide analytically pure CCK-8.

16 Claims, No Drawings

PROCESS FOR THE SOLID PHASE SYNTHESIS OF PEPTIDES WHICH CONTAIN SULFATED TYROSINE

This application is a continuation of application Ser. No. 707,975 filed Mar. 4, 1985 and now abandoned and which is a continuation-in-part of application Ser. No. 607,485, filed May 7, 1984 and now abandoned.

BACKGROUND OF THE INVENTION

This invention relates generally to a process for the preparation of peptides and peptide amides which contain sulfated tyrosine and more specifically to the solid phase synthesis of cholecystokinin (26-33), herein referred to as CCK-8, which has the following structure:

Ondetti and Pluscec (J. Am. Chem. Soc., 92, 195, (1970); J. Med. Chem., 13, 349 (1970); see also: U.S. Pat. Nos. 3,723,406; 3,778,429; 3,835,315; and 3,892,726) synthesized CCK-8 and a series of analogs by the methods of solution phase peptide chemistry, and found that CCK-8 as well as some analogs have a considerably higher potency than the parent molecule, CCK-33. When administered in doses of ca. $10^{-6}$ mg/kg, CCK-8 is a useful diagnostic agent for the examination of the contraction of the gall bladder and of pancreatic secretion (cf. U.S. Pat. No. 3,892,726). Investigations have also revealed that CCK-8 exerts a strong releasing action on the muscle sphincter Oddii; and thus, can be used with good results to alleviate the spasms occurring after gall bladder operations (Ondetti, Rubin, and Engel, J. Am Digestive Diseases, 15, 149 1970). More recent investigations have shown that CCK-8 exerts a strong anorectic effect (Crawley, Rojas-Ramirez, and Mendelson, Peptides, 3, 535 (1982) and references therein).

Ondetti and Pluscec (see references above) described a process for the preparation of CCK-8 from the protected octapeptide amide which was obtained from intermediate compounds prepared by the known methods of solution phase peptide chemistry. Overall yields reported for CCK-8 by these authors were in the range of 1-2% based on the starting phenylalanine amide. By a somewhat modified procedure, Penke, et al., (U.S. Pat. No. 4,102,878) described a process whereby CCK-8 was produced in 6.5% overall yield from phenylalanine amide by the known methods of solution phase peptide chemistry through an improved sulfation procedure. Sipos, U.S. Pat. No. 3,714,140 discloses the solid phase synthesis of peptides and gives as an example the synthesis of CCK-8. However, it is believed that CCK-8 cannot be synthesized by the Sipos method. For example, the cleavage reagent employed (Example 1B, HBr in trifluoroacetic acid/dichloromethane) generates C-terminal peptide acids not C-terminal peptide amides as is CCK-8. In addition, no mention was made as to how the peptide was sulfated or when. A method for the solid phase synthesis of the C-terminal fragments Asp-Phe-NH$_2$ and Trp-Met-Asp-Phe-NH$_2$ of CCK-8 has appeared (Gaudreau, et al., In "Peptides: Synthesis - Structure - Function" (Rich and Gross, eds.), pp. 193-195, Pierce Chemical Company, Rockford, Ill., 1981). Although the Gaudreau, et al., method does not describe the synthesis of CCK-8, it does point out some of the inherent problems associated with a synthesis of CCK-8 by the solid phase method. For example, when Boc-Trp(For)-Met-Asp(OPa)-Phe-OCH$_2$-Resin, where Boc is tert-butyloxycarbonyl, For is formyl, and OPa is phenacyl ester, was treated successively with 0.1M hydrochloric acid in formic acid for Boc removal, 1M sodium thiophenoxide in DMF for OPa removal and 30% ammonia in methanol for For removal and ammonolysis of the peptide from the resin, the major product isolated (60%) was not the desired product but Trp-Met-Asp(Phe-NH$_2$)-NH$_2$ is which PHe-NH$_2$ had been transferred to the beta-carboxyl of Asp while the alpha-carboxyl of Asp had been amidated.

The inventors, in an earlier attempt to develop a solid phase synthesis of unsulfated CCK-8, synthesized the peptide resin Boc-Asp(OtBu)-Tyr-Met-Gly-Trp(For)-Met-Asp(OCH$_2$-PAM-Resin)-Phe-NH$_2$ where OtBu is tert-butyloxy and OCH$_2$-PAM is 4-(oxymethyl)-phenylacetamidomethyl. The peptide was attached to the resin through the beta-carboxyl of Asp. Treatment of the peptide resin with 50% trifluoroacetic acid in dichloromethane for Boc and OtBu removal and then with 10 equivalents of sodium hydroxide in 70% isopropanol for For removal and cleavage of the peptide from the resin resulted in the generation of Asp-Tyr-Met-Gly-Trp-Met-Asp(Phe-NH$_2$)-OH while none of the desired product, Asp-Tyr-Met-Gly-Trp-Met-Asp-Phe-NH$_2$, was detected.

Accordingly, heretofore, no definitive solid phase peptide synthesis of CCK-8 has been described.

We have discovered a process for the synthesis of peptides and peptide amides which provides higher overall yields, for example, 29% CCK-8 after purification to analytical purity in a single chromatographic step.

SUMMARY OF THE INVENTION

In accordance with this invention there is provided a process for the solid phase synthesis of peptides which contain sulfated tyrosine comprising the steps of:

(a) preparing a peptidyl derivative of a resin selected from the group consisting of 4-(X-CH$_2$)phenylacylamido-methyl-polystyrenes and N,4-(X-CH$_2$) phenylacylamidoalkylene-polyacrylamide, where X is halogen or hydroxyl, by the sequential addition of active esters of protected amino acids including tyrosine to an amino acid derivative of said resin, (b) reacting the hydroxyl group of tyrosine with a sulfating agent to provide a sulfate ester, and (c) separating the peptide from the resin by treating the peptidyl derivative with a nucleophile selected from the group consisting of alkalies, ammonia, amines, hydrazines and alkoxides.

The peptide can be purified by ion exchange chromatography.

DETAILED DESCRIPTION

This invention provides a general process for the solid phase synthesis and purification of peptides and peptide amides containing sulfated tyrosine of which CCK-8 is one example. Other examples include the gastrins (G-14-II, G-17-II, and G-34-II), caerulein, phyllocaerulein and the cholecystokinins (CCK-7, CCK-10, CCK-12, and CCK-33).

The choice of temporary protecting groups useful in the solid phase synthesis of sulfated tyrosine containing peptides is dictated by the stability of the sulfate group to the various reagents required for removal of the temporary protecting groups during the synthesis. In this regard, peptides containing sulfated tyrosine are stable at pH≧4, and as expected, exhibit poor stability in liquid HF. It is known, however, that CCK-8 is stable to brief treatment with trifluoroacetic acid (TFA).

The following structure depicts the protecting groups A, B, C, D, and E, to be used in the synthesis of CCK-8:

II

The properties of protecting group E must be such that a terminal amide linkage is generated upon its removal. In addition, group E must also serve as the solid support and be stable to the conditions required for the removal of groups A, B, C, and D as well as conditions for the introduction of the sulfate ester moiety since it will be the last protecting group cleaved to release the product peptide amides.

Peptide amides, of which CCK-8 is an example, are usually synthesized on a diarylmethylamine (benzhydrylamine) support. However, since these supports require liquid HF or similar strong acid treatment for cleavage of the peptide amide from the support, the diarylmethylamine supports are not suitable for the synthesis due to the instability of sulfated peptides to liquid HF. We have found that certain solid supports which allow nucleophilic cleavage of the peptide/solid support anchor bond can be used. Of this type, the X-CH$_2$-polystyrenes or N-X-alkylene-polyacryl-amides are preferred were X is halo or hydroxy. The polyacrylamide supports are less desirable due to their high cost and limited availability. Because Phe-OCH$_2$-polystyrene (derived from ClCH$_2$- or HOCH$_2$-polystyrene) due to steric and electronic factors is known to undergo ammonolytic cleavage only slowly and in low yield to produce Phe-NH$_2$, the X-CH$_2$-polystyrene (X is halo or hydroxy) supports require further alternations to be useful.

The so called handle strategy is particularly useful for altering X-CH$_2$-polystyrene by the attachment of a handle (or spacer linkage) to produce a new solid support whose selective cleavage with nucleophiles, such as ammonia, provides a useful and high yield synthetic process for CCK-8. A number of handles are known in the art, however, we have found that 4-(oxymethyl)-phenylacyl handles and more particularly the 4-(oxymethyl)phenylacetyl handle, are best suited for the solid phase synthesis of CCK-8. The term "phenyl acyl" also includes groups such as -C$_6$H$_4$-(CH$_2$)$_2$CO-and -C$_6$H$_4$-CO-. The phenyl group can be further substituted with a nitro group. The 4-(oxymethyl) phenylacetyl handle when attached to Y-CH$_2$-polystyrene (Y=NH$_2$) provides 4-(oxymethyl)phenylacetamidomethyl-polystyrene (herein referred to as OCH$_2$-PAM-Resin). The term "polystyrene" includes copolymers with minor amounts of other unsaturated monomers such as divinylbenzene. Peptidyl derivatives of the OCH$_2$-PAM-Resin, peptidyl-OCH$_2$-PAM-Resin, can be cleaved by alkalies, ammonia or other amines, hydrazines, or alkoxides to yield respectively the peptide acid, amides, hydrazides, or esters. In addition, the peptidyl-OCH$_2$-PAM-Resin is stable to trifluoroacetic acid (TFA) which is the preferred reagent for tert-butyloxycarbonyl (Boc) and tert-butyloxy (OtBu) protecting group removal and piperidine (PIP) which is the preferred reagent for 9-fluorenylmethyloxycarbonyl (Fmoc) protecting group removal. Thus, the OCH$_2$-PAM-Resin group has the appropriate selectivity to be useful in a total solid phase synthesis of CCK-8 because it is also stable to the reagents required for the sulfation of tyrosine.

Because CCK-8 contains the amino acids aspartic (Asp), tyrosine (Tyr), methionine (Met), and tryptophan (Trp), temporary protecting groups must be selected which minimize potential side reactions known to occur with these amino acids and which are removable under conditions whereby sulfated tyrosine and peptidyl-OCH$_2$-PAM-Resin are stable. Accordingly, the Asp side chain carboxyl protecting groups B and D in structure II may be OtBu because this ester is removable, preferably with TFA, without side reactions.

The selection of protecting group C in II depends on the choice for the temporary amino protecting group A. The Fmoc protecting group is best suited for group A since it is cleavable preferably with piperidine or other bases under conditions whereby the OtBu and OCH$_2$-PAM-Resin groups are stable. In addition, the selection of Fmoc for group A does not require the use of a Trp side chain protecting group (group C), because Trp is stable under Fmoc removal conditions. Under certain conditions, temporary amino protection may be accomplished with the Boc group. However, due to the requirements of orthogonal protection, the Boc group can only be used in the terminal positions of CCK-8 since it cannot be selectively removed in the presence of the OtBu group. Otherwise, the Fmoc group is required for amino protection.

Because the phenolic OH of tyrosine is to be sulfated after the incorporation of tyrosine into the peptide chain, temporary protection of the side chain of tyrosine is not required. However, the use of Tyr with an unprotected phenolic OH in peptide synthesis places special requirements on the coupling methods which may be used. The coupling method of choice in the synthesis of CCK-8 is the active ester method using active esters derived from 2-nitrophenol, 4-nitrophenol, N-hydroxysuccinimide (HOSu), 1-hydroxybenzotriazole (HOBt), or others known in the art. Alternatively, the phenolic OH of tyrosine may be temporarily protected with the tBu group with Fmoc protection of the N-terminal amino group and OtBu protection of the side chain of aspartic acid.

Of the starting materials, namely, Boc-Phe-4-(oxymethyl)phenylacetic acid, aminomethyl- Resin, Fmoc-Asp(OtBu)-OH, Fmoc-Met-OH, Fmoc-Trp-OH, Fmoc-Tyr(tBu)-OH, Fmoc-Gly-OH, and Boc-Asp(OtBu)-OH are well known in the art. The starting material Fmoc-Tyr-OH may be prepared by reacting 9-fluorenylmethyl succinimidyl carbonate (Fmoc-OSu) with tyrosine. The peptides of this invention may be prepared by the sequential addition of the appropriate amino acids one at a time to Boc-Phe-OCH$_2$-PAM-Resin following Boc removal. Such additions are accomplished, for example, by activating the carboxylic acid group in the amino acid to be added after protecting the amino group in such amino acid, for example, by converting it to its Fmoc or Boc derivative, converting this derivative into, for example, an HOBt ester (prepared in situ) and then reacting this active ester with the Phe-OCH$_2$-PAM-Resin or peptidyl-OCH$_2$-PAM-Resin.

Various methods of removing the protecting groups Boc, Fmoc, OtBu, and OCH$_2$-PAM-Resin from the peptide are known in the art. The Boc group may be removed by acid treatment, as by TFA. The Fmoc group may be removed by base treatment, as by piperidine. However, the base selected to remove the Fmoc group must be sufficiently mild as to not cause premature cleavage of the $OCH_2$-PAM-Resin group. The OtBu group may be removed by acid treatment, as by TFA, but not before the sulfation step since acid treatment also removes the N-terminal Boc group which must be present during the sulfation of the tyrosine hydroxyl group. Preferably, the N-terminal amino group may be protected with the Fmoc group which allows removal of the OtBu group prior to sulfation resulting in a process which does not require any acid treatment steps after sulfation which steps can reduce yields due to the instability of the sulfate ester in the acids used for protective group removal.

The sulfation of tyrosine in the protected peptidyl-$OCH_2$-PAM-Resin of this invention may be achieved by the reaction of the protected peptidyl-$OCH_2$-PAM-Resin with sulfur trioxide-pyridine complexes and other sulfur trioxide-tertiary amine complexes, or similar sulfating agents such as pyridinium acetylsulfate, for from 4 to 21 hours at room temperature with excess reagent being filtered off.

Finally, after removal of the Fmoc or Boc and OtBu groups, the C-terminal protecting group $OCH_2$-PAM-Resin may be removed by treatment of the peptide-Resin with an ammoniacal solution, as by ammonia in methanol, to produce the peptide amide. The peptides of this invention may be purified to analytical purity by a single pass down a column containing an ion exchange resin such as DEAE-Trisacryl ™ M (LKB Instruments. Inc.) or a similar ion exchange resin. The DEAE-Trisacryl ion exchange gel is an acrylamide copolymer of N-[Tris-(hydroxymethyl)methyl]-acrylamide and N-2-(diethylamino)ethyl acrylamide. Examples of other ion exchange resins are polysaccharide copolymers such as diethylaminoethyl cellulose and diethylaminoethyl dextran.

The invention will be further illustrated in the following examples. All temperatures are in degrees centigrade unless otherwise stated.

EXAMPLE 1

Fmoc-Tyr-OH

L-Tyrosine (9.06 g, 50 mmol) was dissolved in 100 ml of water and 150 ml of tetrahydrofuran (THF) with 50 ml of 1 N NaOH. To this solution was added Fmoc-OSu (16.87 g, 50 mmol); with rapid stirring. The suspension was adjusted to pH 7 with 1N NaOH and then stirred overnight, after which a small amount of solid tyrosine still remained. Solid citric acid (15 g) was added with stirring followed by 300 ml of ethyl acetate (EtOAc). The EtOAc layer was collected washed with 3×50 ml of 10% citric acid, 4×50 ml of saturated NaCl, and dried over $MgSO_4$. Evaporation of the EtOAc solution gave a light tan syrup which was crystallized from 200 ml of dichloromethane (DCM) to give 18.04 g (89.4% yield) of product (mp 126°–130°).

EXAMPLE 2

Preparation of CCK-8

2A. Boc-Phe-$OCH_2$-PAM-Resin

Boc-Phe-4-(oxymethyl)phenylacetic acid (0.83 g, 2 mmol), where Phe is phenylalanine, dicyclohexylcarbodiimide (DCC) (0.41 g, 2 mmol), and 1-hydroxybenzotriazole (HOBt) (0.46 g, 3 mmol) were dissolved in 50 ml of 4:1 by volume dichloromethane/dimethylformamide (DCM/DMF) with stirring at 0° for 1 hour. Aminomethyl-Resin, where the Resin was a 99:1 by weight styrene divinylbenzene copolymer, (1.34 g, 0.746 meq N/g) was suspended in the filtered reaction mixture (with the precipitated N,N'-dicyclohexylurea (DCU) removed) and shaken for 2 to 15 hours at room temperature. The product Boc-Phe-$OCH_2$-PAM-Resin was isolated by filtration and washed with DCM.

2B. Coupling Steps

2B1. Coupling of Asp (OtBu)

The Boc-Phe-$OCH_2$-PAM-Resin above was suspended and shaken in TFA/anisole/DCM (49:1:50 by volume, 3×50 ml) 10 min each time at room temperature to remove the Boc group. The product was isolated by filtration and washed (3×50 ml each) with DCM, 5% N,N-diisopropylethylamine (DIEA) in DCM, and DCM to give the free base of Phe-$OCH_2$-PAM-Resin.

Fmoc-Asp(OtBu)-OH (1.23 g, 3 mmol), DCC (0.62 g, 3 mmol), and HOBt (0.69 g, 4.5 mmol) were dissolved in 50 ml of 4:1 by volume DCM/DMF with stirring at 0° for 1 hour. Phe-$OCH_2$-PAM-Resin (1 meq assumed) was suspended in the filtered reaction mixture (precipitated DCU removed) and shaken for 2 to 15 hours at room temperature. The product Fmoc-Asp (OtBu)-Phe-$OCH_2$-PAM-Resin was collected by filtration and washed with DCM.

2B2. Coupling of Met

The Fmoc-Asp(OtBu)-Phe-$OCH_2$-PAM-Resin above was suspended and shaken in PIP/DMF (1:4 by volume, 50 ml) for 3 min at room temperature and then a second time for 7 min to remove the Fmoc group. The product was isolated by filtration and washed (3×50 ml each) with DMF and DCM to give the free base of Asp(OtBu)-Phe-$OCH_2$-PAM-Resin.

Fmoc-Met-OH (1.12 g, 3 mmol), DCC (0.62 g, 3 mmol), and HOBt (0.69 g, 4.5 mmol) were dissolved in 50 ml of 4:1 by volume DCM/DMF with stirring at 0° for 1 hour. Asp(OtBu)-Phe-$OCH_2$-PAM-Resin (1 meq assumed) was suspended in the filtered reaction mixture (precipitated DCU removed) and shaken for 2 to 15 hours at room temperature. The product Fmoc-Met-Asp(OtBu)-Phe-$OCH_2$-PAM-Resin was collected by filtration and washed with DCM and DMF.

2B3. Coupling of Trp

The foregoing procedure (Example 2B2) for coupling Met was repeated except that Fmoc-Trp-OH (1.28 g, 3 mmol) was substituted for Fmoc-Met-OH to provide Fmoc-Trp-Met-Asp(OtBu)-Phe-$OCH_2$-PAM-Resin.

2B4. Coupling of Gly

The foregoing procedure (Example 2B2) for coupling Met was repeated except that Fmoc-Gly-OH (0.89 g, 3 mmol; was substituted for Fmoc-Met-OH to provide Fmoc-Gly-Trp-Met-Asp-(OtBu)-Phe-$OCH_2$-PAM-Resin.

2B5. Coupling of Met

The foregoing procedure (Example 2B2) for coupling Met (1.12 g, 3mmol) was repeated to provide Fmoc-Met-Gly-Trp-Met-Asp(OtBu)-Phe-$OCH_2$-PAM-resin.

2B6. Coupling of Tyr

The foregoing procedure (Example 2B2) for coupling Met was repeated except that Fmoc-Tyr-OH (1.21 g, 3 mmol) was substituted for Fmoc-Met-OH to provide Fmoc-Tyr-Met-Gly-Trp-Met-Asp(OtBu)-Phe-$OCH_2$-PAM-Resin.

2B7. Coupling of Asp(OtBu)

The foregoing procedure (Example 2B2) for coupling Met was repeated except that Boc-Asp(OtBu)-OH (derived from its dicyclohexylamine salt, 1.41 g, 3 mmol) was substituted for Fmoc-Met-OH to provide Boc-Asp(OtBu)-Tyr-Met-Gly-Trp-Met-Asp(OtBu)-Phe-OCH$_2$-PAM-Resin.

2C. Sulfation Step

The Boc-Asp(OtBu)-Tyr-Met-Gly-Trp-Met-Asp(OtBu)-Phe-OCH$_2$-PAM-Resin above was washed with DMF/pyridine (2:1 by volume, 3×50 ml), suspended in 60 ml of the same solvent containing sulfur trioxide pyridine complex (6.25 g, 40 mmol), and shaken for 21 hours. The sulfated Boc-Peptidyl-PAM-Resin was collected by filtration and washed with DMF and DCM (3×50 ml each).

2D. Deprotection Step

The Boc-Asp(OtBu)-Tyr (SO$_3$H)-Met-Gly-Trp-Met-Asp(OtBu)-Phe-OCH$_2$-PAM-Resin above was washed with DCM (3×50 ml), suspended and shaken in TFA/anisole/DCM (49:1:50 by volume, 3×50 ml, 10 min each) to remove the Boc and OtBu groups. The sulfated Peptidyl-PAM-Resin was isolated by filtration; washed (3×50 ml each) with DCM, 5% DIEA in DCM, and DCM; and dried in vacuo.

2E. Cleavage Step

The Asp-Tyr-(SO$_3$H)-Met-Gly-Trp-Met-Asp-Phe-OCH$_2$-PAM-Resin above was placed in a pressure bottle, suspended in 200 ml MeOH, saturated with NH$_3$ at −20°, and sealed. The suspension was stirred at room temperature for 2–5 days. After venting the excess NH$_3$, the PAM-Resin was filtered off and washed with MeOH. The combined filtrates were evaporated to dryness to give 1.22 g (105% of the overall theoretical yield) of crude CCK-8.

2F. Purification

The crude product above was dissolved in 20 ml of 0.1 M (NH$_4$)$_2$CO$_3$, and applied to a DEAE-Trisacryl™ M column (2.5×93.4 cm, LKB Instruments, Inc.). Elution of the column with a linear gradient of (NH$_4$)$_2$CO$_3$ produced from 2000 ml each of 0.1M and 1.0M (NH$_4$)$_2$CO$_3$ and pumped at 3 ml/min at 20–70 psi gave pure CCK-8 in fractions 102–114 (21 ml each). The fractions were pooled, concentrated to dryness, diluted with water, and lyophilized to give 0.27 g (23% of the overall theoretical yield) of the ammonium salt of CCK-8, R$_f$(in CMAW on E. Merck Silica gel 60 F-245) =0.26. CMAW is 9 parts chloroform, 3 parts methanol, 1 part acetic acid and 1 part water by volume.

EXAMPLE 3

Preparation of CCK-8, Preferred Method

3A. Boc-Phe-OCH$_2$-PAM-Resin

Boc-Phe-4-(oxymethyl) phenylacetic acid (0.83 g, 2 mmol; where Phe is phenylalanine), dicyclohexylcarbodiimide (DCC, 0.41 g, 2 mmol), and 1-hydroxybenzotriazole (HOBt, 0.46 g, 3 mmol) were dissolved in 50 ml of 4:1 by volume dichloromethane/dimethylformamide (DCM/DMF) with stirring at 0° C. for 1 hour. Aminomethyl-Resin (1.34 g, 0.746 mmol N/g, where the Resin was a 99:1 by weight styrene-divinylbenzene copolymer) was suspended in the filtered reaction mixture (with the precipitated N,N'-dicyclohexylurea (DCU) removed) and shaken for 2 to 15 hours at room temperature. The product Boc-Phe-OCH$_2$-PAM-Resin was isolated by filtration and washed with DCM.

3B. Fmoc-Asp(OtBu)-Phe-OCH$_2$-PAM-Resin

The Boc-Phe-OCH$_2$-PAM-Resin above was suspended and shaken in TFA/anisole/DCM (49:1:50 by volume, 3×50 ml) 10 min each time at room temperature to remove the Boc group. The product was isolated by filtration and washed (3×50 ml each) with DCM, 5% N,N-diisopropylethylamine (DIEA) in DCM, and DCM to give the free base of Phe-OCH$_2$-PAM-Resin.

Fmoc-Asp(OtBu)-OH (1.23 g, 3 mmol), DCC (0.62 g, 3 mmol), and HOBt (0.69 g, 4.5 mmol) were dissolved in 50 ml of 4:1 by volume DCM/DMF with stirring at 0° for 1 hour. Phe-OCH$_2$-PAM-Resin (1 meq assumed) was suspended in the filtered reaction mixture (precipitated DCU removed) and shaken for 2 to 15 hours at room temperature. The Fmoc-Asp-(OtBu)-Phe-OCH$_2$-PAM-Resin product was collected by filtration and washed with DCM.

3C. Fmoc-Met-Asp(OtBu)-Phe-OCH$_2$-PAM-Resin

The Fmoc-Asp(OtBu)-Phe-OCH$_2$-PAM-Resin above was suspended and shaken in PIP/DMF (1:4 by volume, 50 ml) for 3 min at room temperature and then a second time for 7 min to remove the Fmoc group. The product was isolated by filtration and washed (3×50 ml each) with DMF and DCM to give the free base of Asp(OtBu)-Phe-OCH$_2$-PAM-Resin.

Fmoc-Met-OH (1.12 g, 3 mmol), DCC (0.62 g, 3 mmol), and HOBt (0.69 g, 4.5 mmol) were dissolved in 50 ml of 4:1 by volume DCM/DMF with stirring at 0° for 1 hour. Asp(OtBu)-Phe-OCH$_2$-PAM-Resin (1 meq assumed) was suspended in the filtered reaction mixture (precipitated DCU removed) and shaken for 2 to 15 hours at room temperature. The Fmoc-Met-Asp-(OtBu)-Phe-OCH$_2$-PAM-Resin product was collected by filtration and washed with DCM and DMF.

3D. Fmoc-Asp(OtBu)-Tyr(tBu)-Met-Gly-Trp-Met-Asp(OtBu)-Phe-OCH$_2$-PAM-Resin

The Fmoc-Met-Asp(OtBu)-Phe-OCH$_2$-PAM-Resin above was deprotected and coupled sequentially with Fmoc-Trp-OH (1.28 g, 3 mmol), Fmoc-Gly-OH (0.89 g, 3 mmol), Fmoc-Met-OH (1.12 g, 3 mmol), Fmoc-Tyr(-tBu)-OH (1.37 g, 3 mmol), and Fmoc-Asp(OtBu)-OH (1.23 g, 3 mmol) as exemplified in Example 2C to provide Fmoc-Asp(OtBu)-Tyr(tBu)-Met-Gly-Trp-Met-Asp(OtBu)-Phe-OCH$_2$-PAM-Resin.

3E. OtBu and tBu removal

The Fmoc-Asp(OtBu)-Tyr(tBu)-Met-Gly-Trp-Met-Asp(OtBu)-Phe-OCH$_2$-PAM-Resin above was washed with DCM (3×50 ml), suspended and shaken in TFA/anisole/DCM (49:1:50 by volume, 3×50 ml,. 10 min each) to give Fmoc-Asp-Tyr-Met-Gly-Trp-Met-Asp-Phe-OCH$_2$-PAM-Resin which was isolated by filtration; washed (3×50 ml each) with DCM, 5% DIEA in DCM, and DCM.

3F. Sulfation

The Fmoc-Asp-Tyr-Met-Gly-Trp-Met-Asp-Phe-OCH$_2$-PAM-Resin above was washed with DMF/pyridine (2:1 by volume, 3×50 ml), suspended in 60 ml of the same solvent containing sulfur trioxide-pyridine complex (6.36 g, 40 mmol), and shaken for 21 hours to provide Fmoc-Asp-Tyr(SO$_3$H)-Met-Gly-Trp-Met-Asp-Phe-OCH$_2$-PAM-Resin which was collected by filtration and washed with DMF and DCM (3×50 ml each).

3G. Fmoc Removal

The Fmoc-Asp-Tyr-SO$_3$H)-Met-Gly-Trp-Met-Asp-Phe-OCH$_2$-PAM-Resin above was washed DMF (3×50 ml), suspended and shaken in PIP/DMF (1:4 by volume, 50 ml) for 3 min and then a second time for 7 min, to give Asp-Tyr(SO$_3$H)-Met-Gly-Trp-Met-Asp-Phe-OCH$_2$-PAM-Resin which was washed (3×50 ml each) with DMF, DCM, 5% DIEA in DCM, and DCM and dried in vacuo.

2H. Resin Cleavage

The Asp-Tyr(SO₃H)-Met-Gly-Trp-Met-Asp-Phe-OCH₂-PAM-Resin above was placed in a pressure bottle, suspended in 200 ml MeOH, saturated with NH₃ at −20°, and sealed. The suspension was stirred at room temperature for 2-5 days. After venting the excess NH₃, the PAM-Resin was filtered off and washed with MeOH. The filtrate was evaporated to dryness to give 1.38 g (119% of the theoretical yield) of crude CCK-8.

3I. Purification

The crude product above was dissolved in 20 ml of 0.15M NH₄HCO₃, and applied to a DEAE-Trisacryl ™ M column (5.08×23.5 cm, LKB Instruments, Inc.). Elution of the column with a linear gradient of NH₄HCO₃ produced from 2000 ml each of 0.15M and 1.5M NH₄ HCO₃ (PH8) and pumped at 3 ml/min at 20-70 psi gave pure CCK-8 in fractions 117-137 (21 ml each). The fractions were pooled, concentrated to dryness, diluted with 0.1M NH₃, and lyophilized to give 0.33 g (29% of the overall theoretical yield) of the ammonium salt of CCK-8, $R_f$(in CMAW on E. Merck silica gel 60 F-254)=0.26. CMAW is 6 parts chloroform, 3 parts methanol, 1 part acetic acid, and 1 part water by volume.

The foregoing invention provides for the solid phase synthesis of analytically pure peptides containing sulfated tyrosine in overall yields of 3 to 4 times those achieved by previously known processes.

We claim:

1. A process for the solid phase synthesis of peptides which contain sulfated tyrosine comprising the steps of:
   (a) preparing a peptidyl derivative of a resin selected from the group consisting of aminomethyl-polystyrene and N-aminoalkylene-polyacrylamide, by the attachment of a 4-(oxymethyl)phenylacyl handle in the form of its protected amino acid ester derivatives followed by the sequential addition of active esters of protected amino acids including tyrosine to said resin,
   (b) reacting the hydroxyl group of the tyrosine containing peptidyl resin with a sulfur trioxide-tertiary amine complex to provide a sulfate ester which is collected by filtration and washed to remove the excess sulfating agent, and
   (c) separating the peptide from the resin by treating the peptidyl derivative with a nucleophile selected from the group consisting of alkalies, ammonia, amines, hydrazines and alkoxides.

2. The process of claim 1 including the step of purifying the peptide by passing a solution of said peptide through an ion exchange column.

3. The process of claim 1 wherein the resin is aminomethyl-polystyrene.

4. The process of claim 1 wherein the handle is 4-(oxymethyl)phenylacetyl.

5. The process of claim 1 wherein a protected phenylalanine ester derivative of the handle of claim 1 is added as its active ester to the resin.

6. The process of claim 5 wherein active esters of the protected amino acids, aspartic acid, methionine, tryptophan, glycine, methionine, tyrosine, and aspartic acid are sequentially added such that the CCK-8 peptidyl derivative of the resin is produced.

7. The process of claim 1 wherein the complex is pyridine sulfur trioxide.

8. The process of claim 1 wherein the peptide is separated from the resin by treatment of the peptidyl derivative with ammonia.

9. The process of claim 1 wherein the active esters of the protected amino acids are derived from a compound selected from the group consisting of 2-nitrophenol, 4-nitrophenol, N-hydroxysuccinimide and 1-hydroxybenzotriazole.

10. The process of claim 6 wherein the amino group of the amino acid is protected by a group selected from Boc and Fmoc, the side chain carboxyl group of Asp is protected by OtBu and the side chain of Tyr is unprotected.

11. The process of claim 6 wherein the amino group of the amino acid is protected by a group selected from Boc and Fmoc, the side chain carboxyl group of Asp is protected by OtBu and the side chain hydroxyl of Tyr is protected by tBu.

12. The process of claim 1 wherein the peptidyl derivative has the formula:

A—Asp(OtBu)—Tyr—Met—Gly—Trp—Met—Asp(OtBu)—Phe—OCH₂—PAM—Resin wherein A is an amino protecting group selected from the group consisting of Boc and Fmoc.

13. The process of claim 12 wherein A is Boc and the Boc and OtBu protective groups are removed after preparation of the sulfate ester.

14. The process of claim 12 wherein A is Fmoc, the OtBu protective groups are removed prior to preparation of the sulfate ester and the Fmoc protective group is removed after preparation of the sulfate ester.

15. The process of claim 1 wherein the peptidyl derivative has the formula:

Fmoc—Asp(OtBu)—Tyr(tBu)—Met—Gly—Trp—Met—Asp(OtBu)—Phe—OCH₂—PAM—Resin and wherein the OtBu and tBu groups are removed prior to preparation of the sulfate ester and the Fmoc group is removed after preparation of the sulfate ester.

16. A process for the solid phase synthesis of CCK-8 comprising the steps of:
   (a) preparing a peptidyl derivative of an aminomethyl-polystyrene resin by the attachment of a 4-(oxymethyl)phenylacetyl handle to said resin in the form of a protected, activated ester derivative of phenylalanine followed by the sequential addition of protected active ester derivatives of aspartic acid, methionine, tryptophan, glycine, methionine, tyrosine, and aspartic acid such that said peptidyl derivative has the formula;

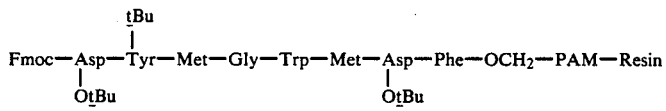

(b) treating said peptidyl derivative with acid so as to remove the OtBu and tBu protective groups;
(c) reacting said peptidyl derivative with sulfur trioxide-pyridine complex so as to form the sulfate ester of tyrosine which is collected by filtration and washed to remove the excess complex;
(d) treating the sulfated peptidyl derivative with base so as to remove the Fmoc protective group, and
(e) treating the sulfated peptidyl derivative with ammonia so as to separate CCK-8 from the resin and handle.

* * * * *